(12) United States Patent
Spiteri et al.

(10) Patent No.: US 10,390,804 B2
(45) Date of Patent: Aug. 27, 2019

(54) SAMPLE COLLECTION

(71) Applicant: UNIVERSITY HOSPITALS OF NORTH MIDLANDS NATIONAL HEALTH SERVICE TRUST, Stoke-on-Trent (GB)

(72) Inventors: Monica Silverstone Spiteri, Stoke-on-Trent (GB); Neil Patel, Loughborough (GB)

(73) Assignee: NEPESMO LIMITED, London (GB)

( * ) Notice: Subject to any disclaimer, the term of this patent is extended or adjusted under 35 U.S.C. 154(b) by 197 days.

(21) Appl. No.: 15/320,690

(22) PCT Filed: Jun. 23, 2015

(86) PCT No.: PCT/GB2015/051820
§ 371 (c)(1),
(2) Date: Dec. 20, 2016

(87) PCT Pub. No.: WO2015/198030
PCT Pub. Date: Dec. 30, 2015

(65) Prior Publication Data
US 2017/0215850 A1    Aug. 3, 2017

(30) Foreign Application Priority Data

Jun. 23, 2014 (GB) .................................. 1411139.7

(51) Int. Cl.
*A61B 10/00* (2006.01)
*A61J 19/02* (2006.01)
(Continued)

(52) U.S. Cl.
CPC .......... *A61B 10/0051* (2013.01); *A61J 19/02* (2013.01); *A61M 1/0019* (2013.01);
(Continued)

(58) Field of Classification Search
CPC .......... A61B 10/0051; A61B 10/0096; A61M 1/0056; A61J 19/00; A61J 19/02; A61J 19/04; G01N 1/4005; G01N 1/34
See application file for complete search history.

(56) References Cited

U.S. PATENT DOCUMENTS 706,465 A     8/1902 Legier
1,647,562 A   11/1927 Drew
(Continued)

FOREIGN PATENT DOCUMENTS

GB    185 807 A    9/1922
GB    243 257 A   11/1925
(Continued)

OTHER PUBLICATIONS

UK Search Report dated Jan. 28, 2015 for GB1411139.7. UK Search Report dated Jan. 28, 2015 for GB1411139.7. UK Search Report dated Jan. 28, 2015 for GB1411139.7. International Search Report dated Oct. 16, 2015 for PCT/GB2015/051820.

*Primary Examiner* — David J. McCrosky
(74) *Attorney, Agent, or Firm* — Shumaker, Loop & Kendrick, LLP

(57) ABSTRACT

Sample collection apparatus and methods of sample collection are provided, for example saliva collection apparatus and methods of saliva collection. Said apparatus conveniently comprises a filter assembly and an interface for delivering material from the apparatus to an assay unit.

14 Claims, 9 Drawing Sheets

(51) Int. Cl.
    *A61M 1/00*     (2006.01)
    *G01N 1/40*     (2006.01)
    *G01N 1/34*     (2006.01)
    *A61B 50/30*     (2016.01)
    *A61C 17/06*     (2006.01)

(52) U.S. Cl.
    CPC ........ *A61M 1/0021* (2013.01); *A61M 1/0056* (2013.01); *A61B 10/0096* (2013.01); *A61B 2050/3008* (2016.02); *A61C 17/04* (2013.01); *G01N 1/34* (2013.01); *G01N 1/4005* (2013.01)

(56) References Cited

U.S. PATENT DOCUMENTS

| | | | |
|---|---|---|---|
| 4,768,238 A | | 9/1988 | Kleinberg et al. |
| 4,771,486 A | | 9/1988 | Gutierrez et al. |
| 5,268,148 A | * | 12/1993 | Seymour ............ A61B 10/0051 422/401 |
| 2004/0184954 A1 | | 9/2004 | Guo et al. |
| 2005/0112024 A1 | | 5/2005 | Guo et al. |
| 2008/0153078 A1 | * | 6/2008 | Braman .................. B01L 3/502 435/2 |
| 2011/0028863 A1 | | 2/2011 | Butlin et al. |
| 2012/0046574 A1 | | 2/2012 | Skakoon |
| 2012/0325721 A1 | | 12/2012 | Plante et al. |
| 2013/0025691 A1 | | 1/2013 | Muir et al. |
| 2014/0294698 A1 | | 10/2014 | Hershey et al. |

FOREIGN PATENT DOCUMENTS

| | | |
|---|---|---|
| GB | 428 554 A | 5/1935 |
| GB | 2 218 338 A | 11/1989 |
| WO | 2013/043109 A3 | 3/2013 |

* cited by examiner

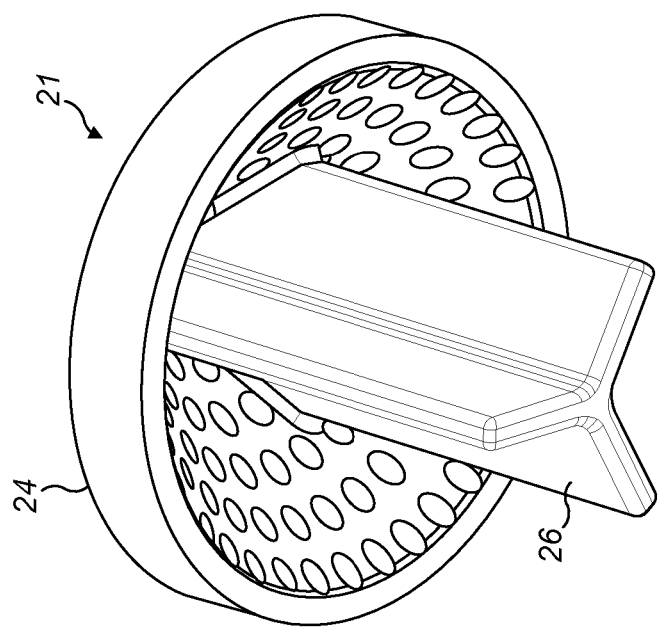
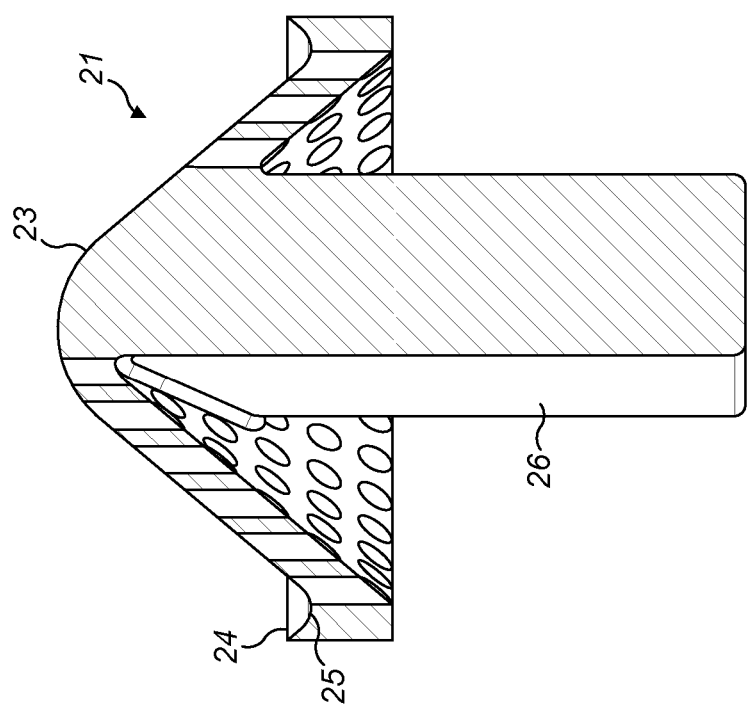

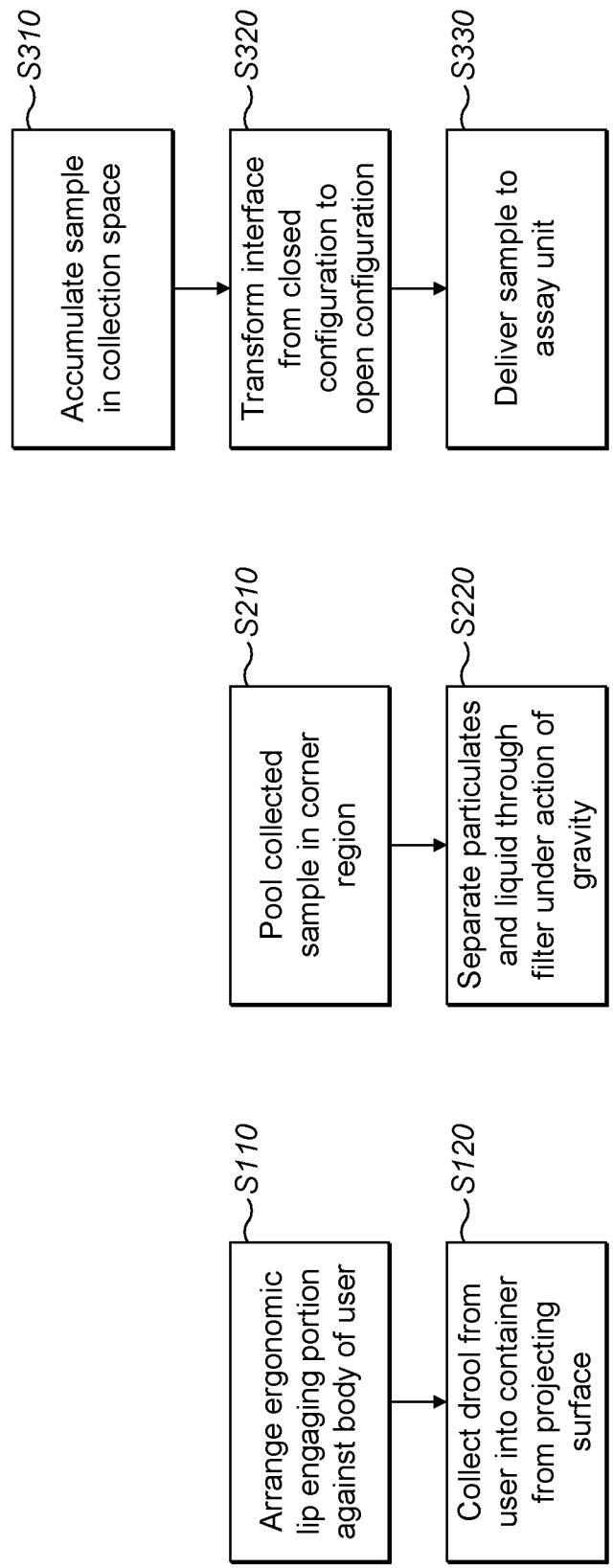

SAMPLE COLLECTION

FIELD OF THE INVENTION

The present invention relates to sample collection apparatus and methods of sample collection, for example saliva collection apparatus and methods of saliva collection.

The present invention relates to filter assemblies, and to methods of filtering, for example to filter assemblies and methods of filtering suitable for use in filtering collected samples of saliva.

The present invention relates to a sample collection apparatus comprising an interface for delivering material from the apparatus to an assay unit, and to methods using the same.

BACKGROUND TO THE INVENTION

Collecting a sample of oral fluid, for example a sample of saliva from an individual is typically performed by having the individual drool into a specimen container or blow a sample down a straw into a generic specimen container.

The dimensions of typical specimen containers are generally not suited to collection of drool, for example by providing a only narrow opening to receive the sample, and/or by comprising features which make interfacing with the body of the individual providing the sample more difficult, such as a circular opening with a thread for retaining a lid on the container after the sample has been delivered. Larger specimen containers with large size openings into which drooling may take place are available, but the distribution of a sample, which may only be of small volume, across the interior surface of a larger specimen container can make it difficult to determine whether a sufficient amount of drool has been provided.

The straw technique is also not particularly easy to perform, requiring coordination of straw and sample container, and typically also introducing unwanted bubbles into the sample.

Example embodiments of the present invention aim to address at least one disadvantage associated with the prior art apparatus and methods, whether identified herein or otherwise, e.g. in aiding the collection of a sample of saliva by drooling.

In performing medical analysis on a sample, for example a sample of saliva, there must be sufficient material in the sample to enable the analysis to be performed. Samples of saliva generally comprise of a liquid element with suspended particulates therein, and it is desirable to separate the liquid element from the particulates for delivery to an analyser. This is so that the particulates do not interfere with the analysis by contamination of sensors, impeding flow through or contact with the sensor assemblies etc. Centrifugation and/or filtration techniques can be used to perform separation of liquid from particulates. Centrifugation is expensive and the equipment for performing centrifugation is not generally transportable, meaning that it is unsuitable for point-of-care testing, near the patient or by the patient themself. Effective filtration may take a relatively long time to perform. With both techniques there are issues when working with only a small amount of material in a sample, so that wastage or loss of material is to be reduced.

Example embodiments of the present invention aim to address at least one disadvantage associated with the prior art apparatus and methods, whether identified herein or otherwise, e.g. in aiding the separation of a sample of saliva through use of a filter assembly.

A sample of saliva, once collected in a suitable specimen container, is normally transferred into a further vessel for delivery to assay equipment. The amount of material required by the assay equipment may be relatively small, but it is important that the sample is not contaminated during collection or transfer and that if there is only a small amount of sample available that loss of sample material is avoided.

Example embodiments of the present invention aim to address at least one disadvantage associated with the prior art apparatus and methods, whether identified herein or otherwise, e.g. in aiding the collection of a sample and its proper delivery to an assay unit without undue delay, loss or contamination.

SUMMARY OF INVENTION

According to the present invention there is provided a sample collection apparatus and a method of sample collection, for example a saliva collection apparatus and a method of saliva collection. Other, optional, features of the invention will be apparent from the dependent claims, and the description which follows.

There now follows a summary of various aspects and advantages according to embodiments of the invention. This summary is provided as an introduction to assist those skilled in the art to more rapidly assimilate the detailed discussion herein and does not and is not intended in any way to limit the scope of the claims that are appended hereto.

In one example there is provided a sample collection apparatus comprising an open ended container to receive a sample, and characterised by a projecting surface that extends generally outwardly and upwardly from the open end of the container to form an ergonomic lip engaging portion.

In this document, the term lip is used to encompass both the lip itself, and also the region of the body below the lip between the lip and the chin. Hence an ergonomic lip engaging portion is in use to engage this area of the body.

In one example the lip engaging portion is arranged to aiding the collection of a sample of saliva by drooling.

In one example the open end comprises a first portion from which the projecting surface extends, and a second portion from which it does not extend, such that the second portion is generally inward of projecting surface and generally there-below.

In one example the projecting surface provides a contact region of the lip engaging portion, arranged in use to contact the body of a user. In one example the projecting surface provides a contact region of the lip engaging portion, arranged in use to contact the body of a user, the contact region comprising a non convex outer edge. In one example the projecting surface provides a contact region of the lip engaging portion, arranged in use to contact the body of a user, the contact region comprising a straight, or a concave outer edge. In one example the projecting surface provides a contact region of the lip engaging portion, arranged in use to contact the body of a user, the contact region comprising a concave outer edge, when viewed from above. In one example the projecting surface provides a contact region of the lip engaging portion, arranged in use to contact the body of a user, the contact region comprising a concave outer edge, when viewed downwardly, i.e. in a direction into the open end of the container.

In one example the projecting surface provides a funnelling region of the lip engaging portion, arranged in use to funnel sample material downward, toward the open end of the container. In one example the funnelling region is provided as a dip in the projecting surface. In one example the funnelling region is provided as a channel in the projecting surface. In one example the funnelling region is provided between wings angled at the sides of the projecting surface. In one example the funnelling region is provided between wings angled upward at the sides of the projecting surface.

In one example the centre of the contact region is aligned with the centre of the funnelling region. In one example the concavity of the contact region transitions into the funnelling region of the lip engaging portion such that material passed onto the projecting surface at the contact region is funnelled there-from by the funnelling region.

In one example the contact region is symmetrical about a median plane of the sample collection apparatus. In one example the funnelling region is symmetrical about a median plane of the sample collection apparatus.

In one example embodiment the projecting surface is symmetrical about a median plane of the sample collection apparatus. In one example embodiment the projecting surface is symmetrical about a median plane of the sample collection apparatus, such that the median plane of the sample collection apparatus is arrangeable in use to contact the body of a user in alignment with a median plane of the body of the user.

In one example embodiment the projecting surface comprises a roll-top edge. In one example embodiment the roll-top edge terminates with a downward sloping extremity, for example a downward slope at one or more of: the first portion, the second portion, the contact region, the funnelling region, and the wings. In one example embodiment the roll-top edge terminates with an outward slope, for example an outward slope at one or more of: the first portion, the second portion, the contact region, the funnelling region, and the wings.

In one example embodiment the projecting surface comprises a saddle point. In one example embodiment the projecting surface comprises a saddle point at a convexity of the roll-top edge and a concavity of the funnelling region. In one example embodiment the saddle point is provided on a median line of the projecting surface.

In one example embodiment the projecting surface extends from the open end, said open end being generally circular when viewed from above.

In one example the projecting surface comprises a low-friction surface, such as a polished area, or a coating, to inhibit adhesion of sample material thereto. In one example the projecting surface comprises a plastics material. In one example the projecting surface comprises an extension of a wall of the container, for example an outer wall of the container. In one example the projecting surface comprises an extension of a cylindrical wall of the container.

In one example the sample collection apparatus comprising an open ended container to receive a sample from a user, by the user drooling onto the projecting surface while the lip engaging portion is against the body, for example lip, of the user.

In one example the sample collection apparatus comprising an open ended container to receive a sample from a user, by the user drooling onto the projecting surface while the lip engaging portion is against the lip of the user, or against the body of the user between the lip and chin of the user.

In one example there is provided a method of sample collection using a sample collection apparatus comprising an open ended container to receive a sample from a user, the method comprising:

arranging a projecting surface, that extends generally outwardly and upwardly from the open end of the container to form an ergonomic lip engaging portion, against the body of the user at or below the lip of the user; and collecting drool from the user, into the container, from the projecting surface.

In one example the method of sample collection is performed using a sample collection apparatus substantially as described in the examples herein.

In one example the method comprises arranging a contact region of the lip engaging portion in contact with the body of a user.

In one example the method comprises arranging a median plane of the sample collection apparatus to contact the body of a user in alignment with a median plane of the body of the user.

In one example the method comprises arranging an open ended container to receive a sample from a user, by the user drooling onto the projecting surface while the lip engaging portion is against the body of the user.

In one example the method comprises arranging an open ended container to receive a sample from a user, by the user drooling onto the projecting surface while the lip engaging portion is against the lip of the user, or against the body of the user between the lip and chin of the user.

In one example there is provided a filter assembly for use in filtering samples of saliva, the filter assembly comprising a first filter element arranged to separate relatively large particulate matter from a sample, by action of gravity drawing the relatively smaller particulate matter and liquid components through the first filter element, characterised in that the first filter element comprises an upwardly angled first filter surface, arranged with a wall, to pool the sample in a corner region between the first filter surface and the wall.

In one example the first filter surface is provided as part of an upwardly extending first filter element. In one example the area on the first filter surface provided by the first filter element is of generally reducing cross section going from the bottom of the first filter element toward the top. In one example the upwardly extending first filter element tapers toward the top. In one example the first filter surface is provided as part of the first filter element as a generally conical or generally frustoconical surface.

In one example the filter assembly is provided in a container, such that with the container resting on a level surface the first filter surface is an upwardly angled first filter surface. In one example the filter assembly comprises an upwardly angled first filter surface which slopes at an angle of 30 degrees to 50 degrees to the vertical, for example approximately 40 degrees. In one example the filter assembly comprises a cone angle of 80 degrees to 120 degrees to the vertical, for example approximately 100 degrees.

In one example embodiment the first filter element comprises a plurality of discrete filter holes. In one example embodiment the first filter element comprises a plurality of substantially identical filter holes. In one example the holes are generally circular. In one example embodiment the first filter element comprises holes of between 0.3 mm and 1.3 mm in diameter, for example between 0.5 mm and 1.1 mm, for example between 0.7 mm and 0.9 mm. In one example embodiment the first filter element comprises holes of 0.8 mm in diameter. In one example embodiment the holes are arranged in a plurality of generally concentric circular groups. In one example embodiment the holes are defined by passageways of between 1 mm and 4 mm in length, for example between 2 mm and 3 mm in length, for example 2.88 mm in length. In one example the ratio of characteristic axial dimension of the passageways to cross sectional dimension is in the region of 3:1 to 4:1, for example 3.6:1. In one example the holes present an opening having an edge which is not aligned with the horizontal, for example an edge which is not aligned with the axial dimension of the passageways. In one example the holes present an opening which comprises an edge which is angled so as to be generally parallel to the first filter surface.

In one example the first filter surface comprises an array of 50 to 150 holes, for example 100 to 140 holes, such as 123 holes. In one example a hole, for example each of the holes in a plurality of holes, comprises between 0.1% and 0.2% of the area of the first filter surface. In one example the first filter element comprises holes that make up between 5% and 30% of the first filter surface, for example between 10% and 20%, such as 16%.

In one example the first filter surface comprises a first group of holes arranged relatively closer to the corner, and a second group of holes arranged relatively further from the corner. In one example the first group of holes comprises a relatively smaller number of holes than the second group of holes. In one example the first filter surface comprises a plurality of groups of holes, for example, two, three or more, with the groups of holes arranged relatively further from the corner region in sequence. In one example the number of holes in a group of holes further from the corner region is fewer than the number of holes in a group relatively closer to the corner. In one example the groups of holes are arranged in a circular pattern, or are grouped into a number of circular patterns. In one example, the holes are arranged with bands of holes running at generally the same distance from the corner, and the bands having more holes per band as the bands approach the corner.

In one example the first filter element is provided as an insert arranged in a container in which the sample is provided. In one example the first filter element and container are arranged, such that inserting the first filter element into the container to an inserted position causes retention of the first filter element in the container. In one example the first filter element and container are arranged, such that pushing the first filter element into the container to an inserted position causes retention of the first filter element in the container. In one example the first filter element and container are arranged, such that inserting the first filter element into the container to an inserted position causes retention of the first filter element in the container. In one example the first filter element and container are arranged, such that inserting the first filter element into the container to an inserted position causes retention of the first filter element in the container. In one example the first filter element comprises a friction fit, or interference fit with the container.

In one example the wall is provided, at least in part, by an opposed portion of the first filter element, providing an upwardly angled surface that extends from the corner region away from the first filter surface.

In one example the wall is provided, at least in part, by a container in which the sample has been collected. In one example the container comprises a wall with which the first filter element can be arranged to provide the corner region between the first filter surface and the wall, at least in part. Part of the corner region may be provided by the opposed portion of the first filter element, in one instance a lower part of the corner region. Part of the corner region may be provided by the wall, in one instance an upper part of the corner region.

In one example the wall is a non-filtering wall. In one example the wall is that of the container, and defines a generally cylindrical interior surface in the region of the first filter element. In one example the wall is provided such that with the container resting on a level surface the wall extends generally upwards vertically.

In one example the corner region comprises an angle of between 70 degrees and 110 degrees, for example approximately 90 degrees. In one example the corner region comprises an angle, for example of less than 170 degrees, or less than 150 degrees, such as for example less than 130 degrees, or less than 110 degrees. In one example the corner region provides an angle of greater than 10 degrees, for example greater than 30 degrees, or greater than 50 degrees, or greater than 70 degrees.

In one example the filter assembly comprises a second filter element. In one example embodiment the first and second filter elements are arranged in the filter assembly such that the output side of the first filter element is in fluid communication with the input side of the second filter element. In one example embodiment the second filter element is arranged to separate relatively small particulate matter from a sample, by action of gravity drawing the liquid component through the second filter element such that only particulate matter below a predetermined threshold remains with the filtered liquid component. In one example embodiment the second filter element comprises a smaller cross sectional area than the first filter element.

In one example the filter assembly is arranged with a buffer volume between the output side of the first filter element and the input side of the second filter element, such that material that passes through the first filter element can accumulate and/or be held in the buffer volume, for example when the rate of passage of material through the first filter element is greater than the rate of passage of material through the second filter element.

In one example the second filter element is made of a porous material. In one example embodiment the second filter element comprises an arrangement of wadding, or of fibres. In one example the wadding, or fibres are made of a material that is itself non-porous.

In one example embodiment the second filter element is located below the first filter element in the container. In one example embodiment the second filter element is provided as an insert arranged in a container in which the sample is provided.

In one example the first filter element, second filter element and container are arranged, such that inserting the first filter element into the container to an inserted position causes retention of the second filter element in the container. In one example the second filter element and container are arranged, such that inserting the second filter element into the container to an inserted position causes retention of the second filter element in the container. In one example the second filter element comprises a friction fit, or interference fit with the container.

In one example embodiment the filter assembly is arranged such that the first filter element contacts the second filter element, to hold the second filter element in place in the filter assembly. In one example embodiment the first filter element comprises a leg extending down below the first filter surface arranged to contact the second filter element and to hold the second filter element in place.

In one example there is provided a method of filtering, the method performed using a filter assembly for filtering samples of saliva, and comprising a first filter element arranged to separate relatively large particulate matter from a sample, by action of gravity drawing the relatively smaller particulate matter and liquid components through the first filter element, the method comprising collecting a sample of saliva, and characterised by pooling the collected sample in a corner region between an upwardly angled first filter surface of the first filter element and a wall.

In one example the method of filtering is performed using a sample collection apparatus substantially as described in the examples herein.

In one example the method of filtering comprises a collection pre-step of sample collection substantially as described in the examples herein.

In one example there is provided a sample collection apparatus comprising a collection space for accumulating a sample, an assay unit and an interface between the collection space and the assay unit; characterised in that the interface is arranged to transform from a closed configuration in which the collection space is isolated from the assay unit to an open configuration in which a sample accumulated in the collection space is delivered to the assay unit.

In one example the collection space and assay unit are arranged relative to one another such that delivery of a sample to the assay unit may take place under the influence of gravity.

In one example the assay unit comprises a region of low pressure, for example a partial vacuum. In one example the assay unit comprises a region of pressure lower than atmospheric pressure. In one example the interface is arranged such that transformation from the closed configuration to the open configuration exposes the low pressure region of the assay unit to the collection space. In one example the interface is arranged such that transformation from the closed configuration to the open configuration exposes a low pressure region of the assay unit to the collection space, such that contents of the collection space are forcibly delivered to the assay unit.

In one example the collection space comprises an outlet passageway and the assay unit comprises an inlet passageway, and the interface is arranged such that transforming from the closed configuration to the open configuration comprises bringing the passageways from an unaligned position to an aligned position.

In one example the collection space and assay container are provided with a seal there-between. In one example the collection space and assay container each interface a sealing element, for example each interface a common sealing element, to isolate one from the other in the closed configuration. In one example the collection space and assay container are provided with a seal there-between to isolate the fluid connection by which a sample is delivered from the collection space to the assay unit from a mechanical connection provided to couple the assay collection space and the assay container.

In one example the collection space and assay unit comprise a mechanical connection by which they are coupled to one another to allow relative rotation. In one example the collection space and assay unit are arranged such that relative rotation there-between transforms their interface from the closed configuration to the open configuration.

In one example the mechanical connection is provided as a snap fit or interference fit. In one example the mechanical connection is provided between a projection and a recess, arranged one on the collection space and the other on the assay container. In one example the collection space and assay unit are demountably coupled one another to separate by elastic deformation of the snap fit or interference fit mechanical connection.

In one example the collection space comprises a ventilation opening by which air from within the collection space may vent. In one example the collection space comprises a ventilation opening which is open to the atmosphere. In one example the collection space comprises a plurality of said ventilation openings.

In one example collection space and assay unit comprise a mechanical connection by which they may be coupled to one another, and further arranged such that effecting mechanical connection of the collection space and assay unit provides a ventilation blocking member to block the ventilation opening. In one example the sample collector comprises a plurality of ventilation openings. In one example the sample collector comprises a ventilation blocking member for each of ventilation opening in a plurality of ventilation openings, such as for all ventilation openings. In one example the assay unit comprises the ventilation blocking member(s).

In one example the mechanical connection is arranged such that sliding of the projection in the interface transforms the interface from the closed configuration to the open configuration. In one example the mechanical connection is arranged such that sliding of the projection in the interface in a first direction transforms the interface from the closed configuration to the open configuration, and that sliding in a second direction transforms the interface from the open configuration to the closed configuration. In one example the first direction and second direction are opposite in sense to each other, for example opposite in rotational sense such as body rotation without axial displacement, or in opposite parallel directions.

In one example the assay unit comprises a frangible sealing member at the interface. In one example the collection space comprises a frangible sealing member at the interface. In one example the interface comprises a frangible sealing member, associated with one of the collection space and assay unit, for example only one of the collection space and the assay unit. In one example the collection space, and/or the assay unit comprises a piercing member arranged to break open a frangible sealing member in transformation of the interface from the closed configuration to the open configuration. In one example the piercing member is arranged to push through the frangible sealing member in transformation of the interface from the closed configuration to the open configuration. In one example the piercing member and interface are arranged to cooperate with one another such that piercing of a frangible sealing member occurs as the collection space and assay unit are pushed together, for example as the collection space and assay unit are being mechanically connected to one another.

In one example the mechanical connection is arranged such that continued sliding of the projection in the interface transforms the interface from the closed configuration to the open configuration, and thereafter transforms the interface back from the open configuration to the closed configuration.

In one example the collection space comprises a container of metered volume and an overflow container. In one example the collection space comprises a plurality of containers of metered volume, for example in combination with a single overflow container. In one example the collection space comprises a plurality of containers of metered volume, and the assay unit comprises a plurality of assay volumes. In one example the metered volumes and assay volumes are provided in corresponding numbers. In one example a metered volume of the collection space comprises an outlet passageway and an inlet passageway of the assay unit is provided as part of an assay volume. In one example the interface is arranged such that transforming from the closed configuration to the open configuration comprises bringing the metered volumes and assay volumes from an unaligned position to an aligned position, such that their respective passageways align with one another to form a fluid connection there-between.

In one example the interface is arranged such that transformation from the closed configuration to the open configuration exposes the low pressure region of the assay unit to the collection space via a lowermost portion of the collection space, such that contents of the lowermost portion are forcibly delivered to the assay unit. In one example the interface is arranged such that transformation from the closed configuration to the open configuration exposes the low pressure region of the assay unit to the collection space via a lower portion of the metered volume, such that contents of the metered volume are forcibly delivered to the assay unit.

In one example the assay unit comprises a transparent material. In one example the assay unit comprises a window through which its content may be viewed or otherwise analysed.

In one example there is provided a sample collection method comprising:

accumulating a sample in a collection space of a sample collection apparatus;

transforming an interface between the collection space and an assay unit from a closed configuration in which the collection space is isolated from the assay unit, to an open configuration; and delivering the sample accumulated in the collection space to the assay unit.

In one example the method of sample collection is performed using a sample collection apparatus substantially as described in the examples herein.

In one example the collection space comprises an outlet passageway and the assay unit comprises an inlet passageway, and the method comprises bringing the passageways from an unaligned position to an aligned position.

In one example the method comprises transforming the interface between the collection space and assay unit by relative motion there-between, for example by relative rotation of the collection space and assay unit.

In one example the method comprises filling a container of metered volume in the collection space with material of the sample, and collecting further material of the sample in an overflow container. In one example the method comprises filling a plurality of containers of metered volume in the collection space with material of the sample, and collecting further material of the sample in an overflow container.

In one example the method comprises delivering material of the sample from the collection space into one, or into a plurality of assay volumes in the assay unit.

In one example method comprises transforming from the closed configuration to the open configuration to bring metered volume(s) and assay volume(s) from an unaligned position to an aligned position, such that respective outlet and inlet passageways thereof connect with one another.

In one example the method comprises accumulating the sample in the collection space under gravity.

In one example the method comprises delivering the sample to the assay unit under gravity.

In one example the method comprises pre-loading the assay unit with a reagent.

In one example the method comprises the mixing of a sample with a reagent in the assay unit.

In one example the method comprises inspecting, or otherwise analysing the content of the assay unit while the sample is contained therein.

In one example the method comprises using a low pressure region in the assay unit to force the sample from the collection space.

In one example the collection space comprises a ventilation opening, and the method comprises blocking the ventilation opening. In one example the assay unit comprises a ventilation blocking member and the method comprises blocking the ventilation opening of the collection unit with the ventilation blocking member. In one example the method comprises blocking the ventilation opening as the collection unit and assay unit are moved relative to one another, such as in the process of coupling the collection space and assay unit to one another.

In one example the method comprises piercing a frangible sealing member provided at the interface. In one example the method comprises piercing a frangible sealing member as the collection unit and assay unit are moved relative to one another, such as in the process of coupling the collection space and assay unit to one another.

In one example there is provided a sample collection apparatus comprising two or three of:

(a) an open ended container to receive a sample, and characterised by a projecting surface that extends generally outwardly and upwardly from the open end of the container to form an ergonomic lip engaging portion;

(b) a filter assembly for use in filtering samples of saliva, the filter assembly comprising a first filter element arranged to separate relatively large particulate matter from a sample, by action of gravity drawing the relatively smaller particulate matter and liquid components through the first filter element, characterised in that the first filter element comprises an upwardly angled first filter surface, arranged with a wall, to pool the sample in a corner region between the first filter surface and the wall; and (c) a sample collection apparatus comprising a collection space for accumulating a sample, an assay unit and an interface between the collection space and the assay unit; characterised in that the interface is arranged to transform from a closed configuration in which the collection space is isolated from the assay unit to an open configuration in which a sample accumulated in the collection space is delivered to the assay unit.

In the aforementioned apparatus there may be additional features as described in relation the apparatus aspects (a), (b) and (c) in the corresponding optional statements above.

In one example there is provided a method of sample collection comprising two or three of:

(i) using a sample collection apparatus comprising an open ended container to receive a sample from a user, the method comprising:

arranging a projecting surface, that extends generally outwardly and upwardly from the open end of the container to form an ergonomic lip engaging portion, against the body of the user at or below the lip of the user; and collecting drool from the user, into the container, from the projecting surface;

(ii) using a filter assembly for filtering samples of saliva, and comprising a first filter element arranged to separate relatively large particulate matter from a sample, by action of gravity drawing the relatively smaller particulate matter and liquid components through the first filter element, the method comprising collecting a sample of saliva, and characterised by pooling the collected sample in a corner region between an upwardly angled first filter surface of the first filter element and a wall; and;

(iii) accumulating a sample in a collection space of a sample collection apparatus;

transforming an interface between the collection space and an assay unit from a closed configuration in which the collection space is isolated from the assay unit, to an open configuration; and delivering the sample accumulated in the collection space to the assay unit.

In the aforementioned method there may be additional steps as described in relation the aspects (i), (ii) and (iii) in the corresponding optional statements above.

BRIEF INTRODUCTION TO DRAWINGS

For a better understanding of the invention, and to show how example embodiments may be carried into effect, reference will now be made to the accompanying drawings in which:

FIGS. 4A and 4B show detail of a first filter element of the sample collection apparatus of FIG. 1A and FIG. 1B;

FIGS. 8A, 8B and 8C show example methods of sample collection, filtering and using a sample collection apparatus respectively.

DESCRIPTION OF EXAMPLE EMBODIMENTS

At least some of the following example embodiments provide an improved sample collection apparatus. Many other advantages and improvements will be discussed in more detail below, or will be appreciate by the skilled person from carrying out example embodiments based on the teachings herein.

Figure 1B:
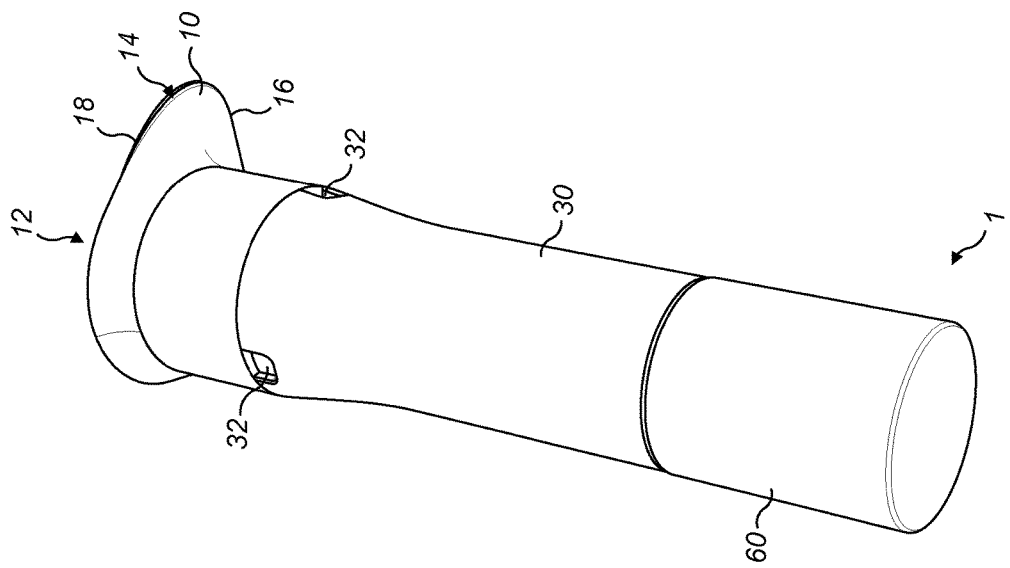
FIGS. 1A and 1B are perspective views of an example sample collection apparatus.
Figure 1A:
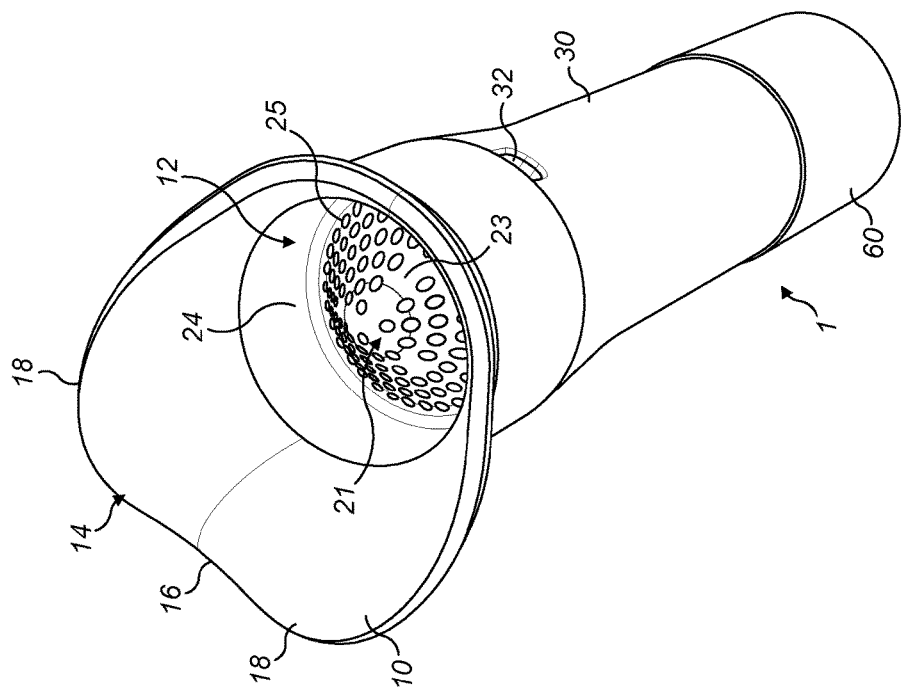

FIGS. 1A and 1B show a schematic view of an example sample collection apparatus 1. The sample collection apparatus 1 comprises an open ended container to receive a sample from the mouth of a user. In a clinical situation the user may be a patient and the sample being collected may comprise saliva to be analysed for clinically relevant characteristics, such as the presence of biomarkers etc. To enable an effective analysis of the sample there are certain requirements around collection of the sample. For example, the collection apparatus should enable a clean, uncontaminated sample to be collected. Once the sample material has been delivered into a sample collection apparatus it is helpful for the sample to be processed by filtration and prepared for analysis. Delivering a suitable amount of sample material in a timely manner and in a way which is convenient for subsequent analysis is also desirable.

The sample collection apparatus 1 of FIGS. 1A and 1B is intended to facilitate collection of a sample, and as such comprises a projecting surface 10 that extends generally outwardly and upwardly from the open end 12 of the container. The projecting surface 10 forms an ergonomic lip engaging portion. The lip engaging portion aids the collection of a sample of saliva by drooling.

A user arranges the lip engaging portion against the lower lip, or in the region just below the lower lip between lip and chin, on the median plane of the body. By allowing saliva to collect in the mouth, and then drooling over the lip, the user can provide saliva into the sample collection apparatus through the open end 12 thereof. This procedure is convenient, as the upward and outward disposition of the lip engaging portion allows drooling into the sample collection apparatus 1 to take place without significant leaning forward of the head of the user. In one example embodiment the projecting surface comprises a roll-top edge.

The sample collection apparatus 1 is intended to be intuitive to use, in the sense that by providing the open end 12 with a portion from which the projecting surface 10 extends, and a separate portion from which the projecting surface 10 does not extend, it can be readily understood by the user where the lip engaging portion is, and where it ought to be positioned in use. As shown in FIGS. 1A and 1B, the portion of the open end 12 from which the lip engaging portion does not extend is arranged generally inward of projecting surface 10 and generally there-below.

For comfort, and to match the shape of the anatomy of a user the projecting surface 10 provides a contact region 14 of the lip engaging portion. This contact region 14 in use contacts the body of a user and in the sample collection apparatus 1 comprises a concave outer edge 16 when viewed downwardly, i.e. in a direction into the open end of the container. A roll-top edge to the projecting surface 10 terminates with a downward sloping extremity at the contact region 14, enhancing comfort as the contact region 14 is in use against the lip.

In order to funnel sample material downward the projecting surface provides a funnelling region of the lip engaging portion toward the open end of the container. The funnelling region is provided as a dip between wings 18 that angle upward at the sides of the projecting surface 10. The centre of the contact region 14 is aligned with the centre of the funnelling region so that the concavity of the contact region 14 transitions into the funnelling region of the lip engaging portion such that material passed onto the projecting surface at the contact region 14 is funnelled there-from by the funnelling region, down toward the open end 12. To aid funnelling the projecting surface 10 comprises a low-friction finish, and the projecting surface transitions smoothly down into the open end as a integral part of the wall of the sample collection apparatus with no step, joining line or similar between the lip engaging portion and the open end 12, or indeed below the open end 12.

Figure 2:
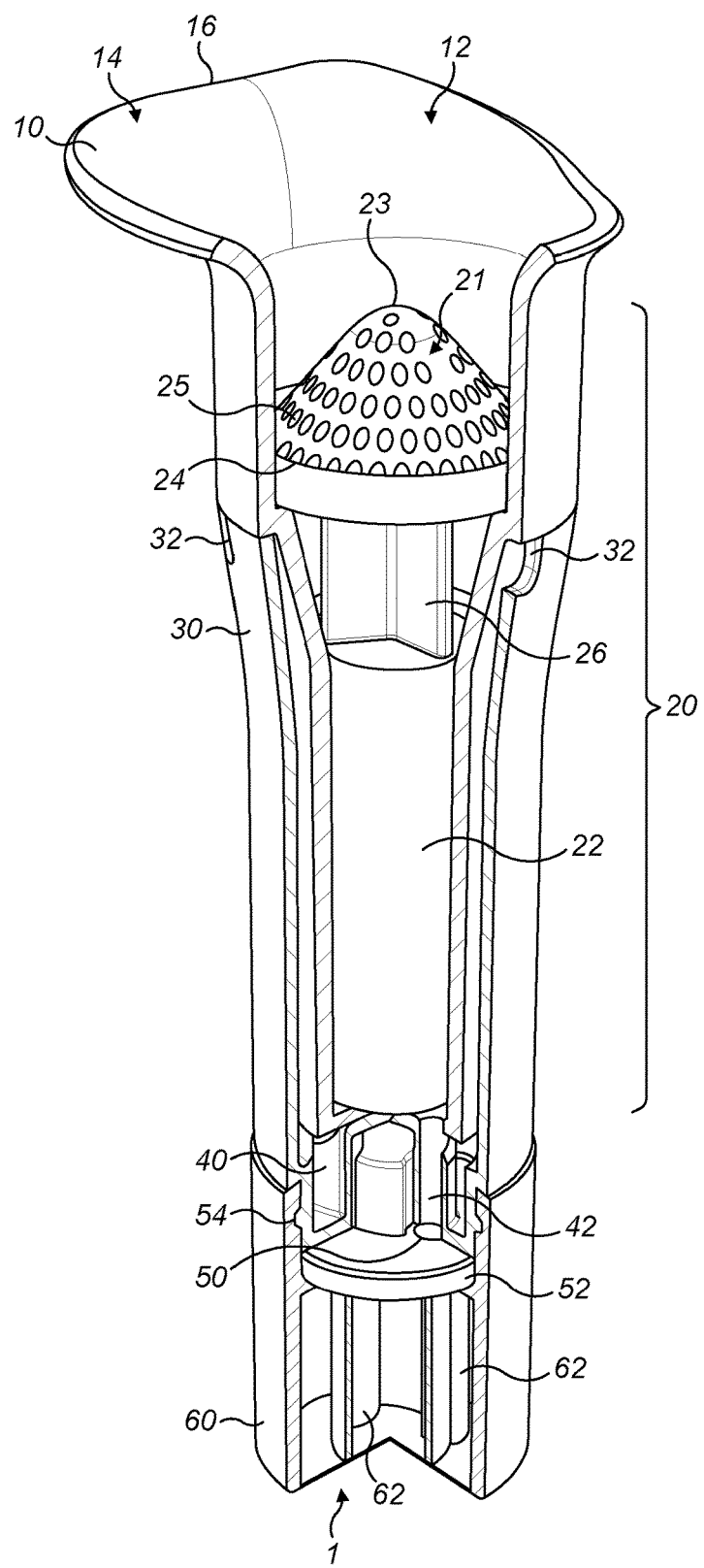
FIG. 2 is a cut-away perspective view of the sample collection apparatus of FIG. 1A and FIG. 1B.
Figure 3C:
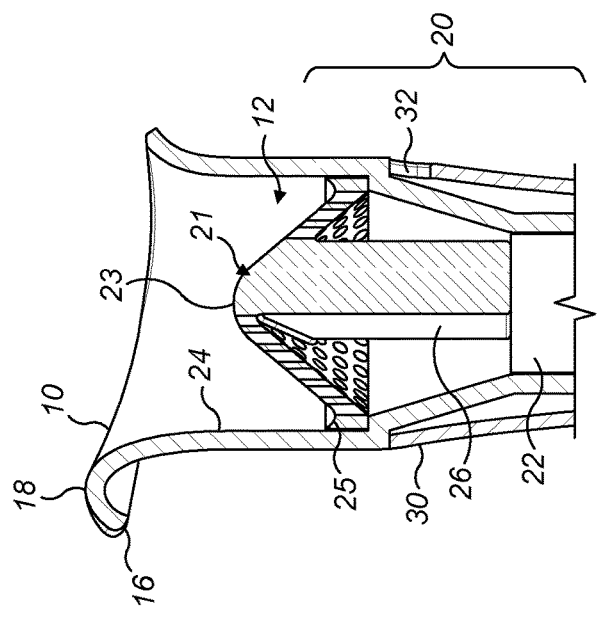
FIGS. 3A, 3B and 3C show detail of a lip engaging portion of the sample collection apparatus of FIG. 1A and FIG. 1B.
Figure 3B:
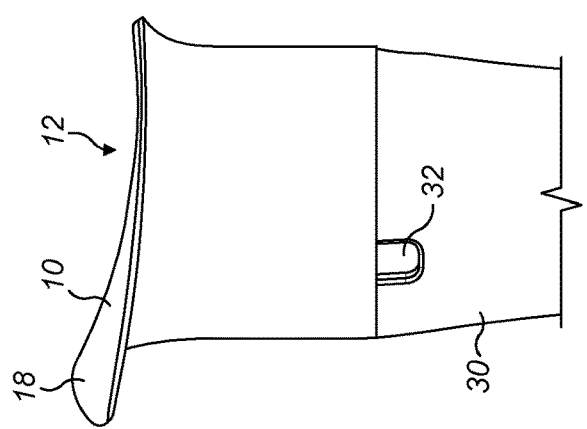
Figure 3A:
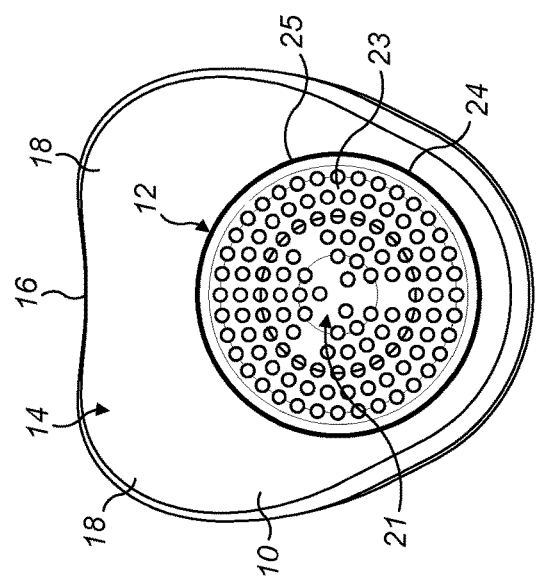
Figure 5A:
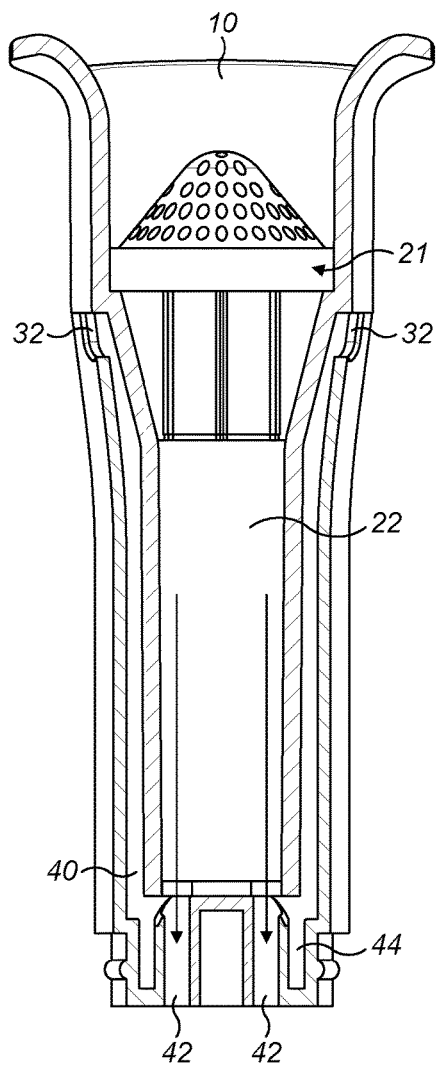
FIGS. 5A through 5D show detail of the a collection space and assay unit of another example sample collection apparatus.
Figure 5B:
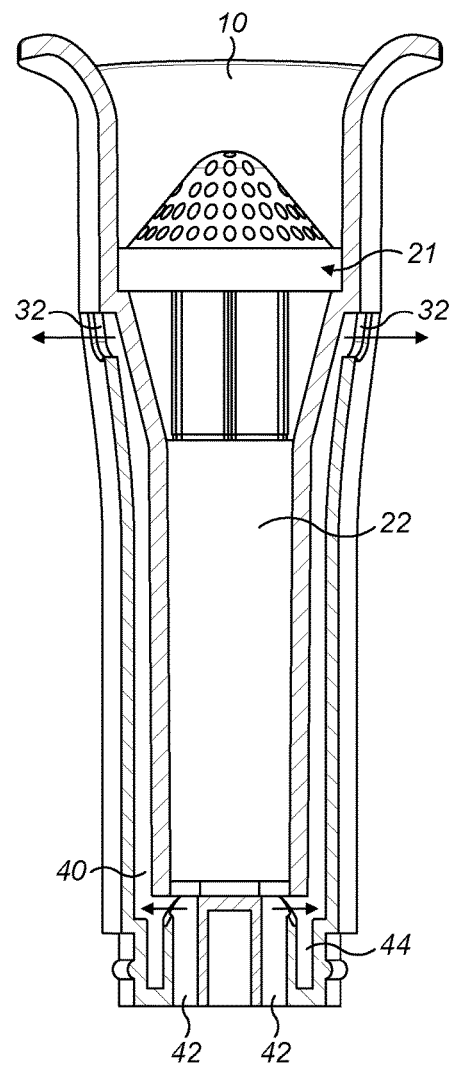
Figure 5D:
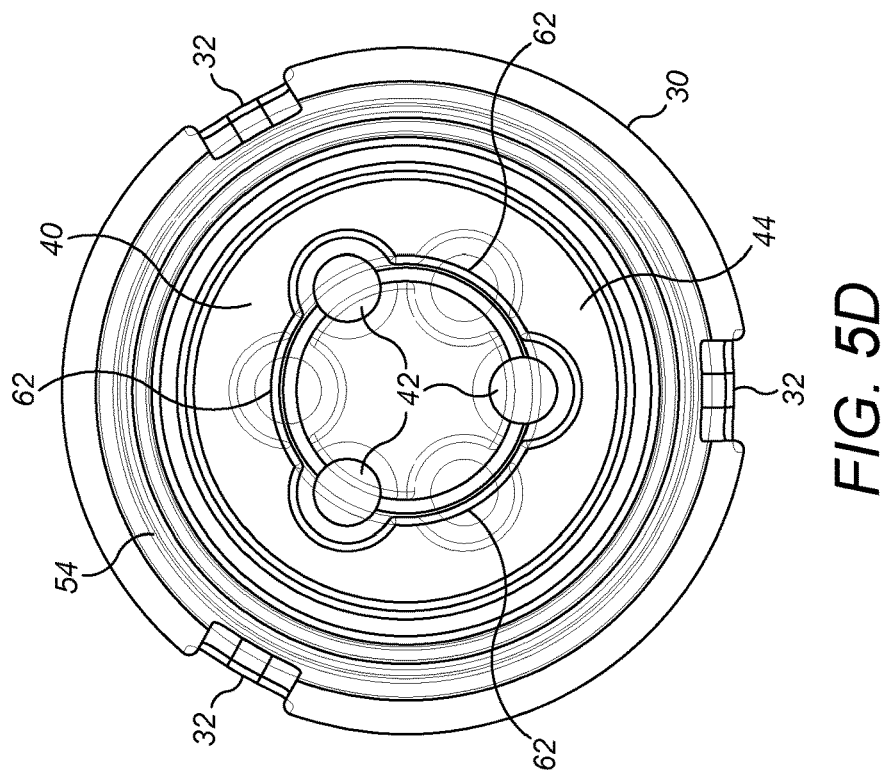
Figure 5C:
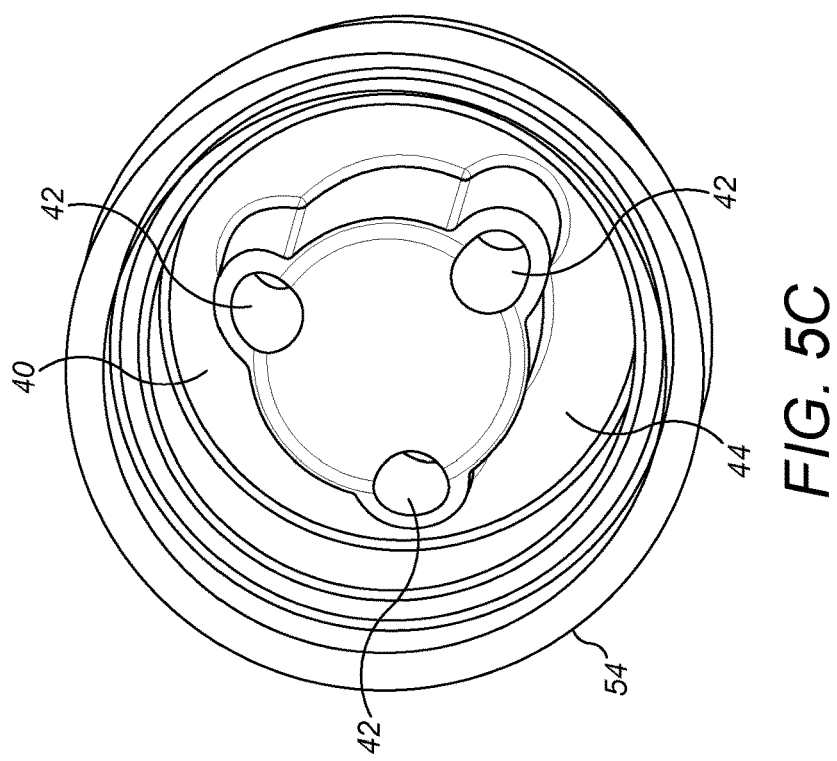

Below the open end 12 is a filter assembly 20 for use in filtering samples of saliva. FIG. 2 shows the filter assembly in more detail in a cut-away perspective view of the sample collection apparatus of FIG. 1A and FIG. 1B. The filter assembly 20 comprises a first filter element 21, also visible in FIG. 1A and FIG. 1B. The first filter element 21 is arranged to separate relatively large particulate matter from a sample, by action of gravity drawing the relatively smaller particulate matter and liquid components there-through. The first filter element 21 comprises an upwardly angled first filter surface 23, arranged with a wall 24. In use the sample being filtered pools in a corner region 25 between the first filter surface 23 and the wall 24.

The wall 24 is provided in part, by an opposed portion of the first filter element 21, providing an upwardly angled surface that extends from the corner region 25 away from the first filter surface 23, and above this region is provided by a container 30 in which the sample has been collected. The corner region 25 comprises an angle of approximately 90 degrees.

The first filter element 21 tapers toward the top such that the first filter surface 23 comprises a generally conical surface. With the container resting on a level surface the first filter surface 23 upwardly angled with a cone angle of approximately 40 degrees. The first filter element 21 comprises a plurality of discrete filter holes that are each of 0.8 mm in diameter. The holes are arranged in a plurality of generally concentric circular groups with 123 holes shown in total in the embodiment of FIGS. 1-4. FIG. 4A and FIG. 4B show the first filter element 21 in more detail. The holes are at the ends of passageways of 2.88 mm in length. In this way, the ratio of the characteristic axial dimension of the passageways to cross sectional dimension is 3.6:1, which has been found to enable efficient filtering of typical particulate contaminants in material having the general consistency of saliva.

To aid passage of liquid through the holes the holes present an opening having an edge which is not aligned with the horizontal, in this case parallel to the first filter surface. This enables liquid to start passing down through the hole and into the passageway as it runs down the first filter surface as it first encounters a hole edge. The whole of the hole does not need to be wetted, and in fact the angled edge aids ventilation from below the first filter element for periods of filtration where the entirety of the passageway is not occluded with liquid/particles. To further improve transit of the liquid components of the saliva through the first filter element 21 while removing typical particulate contaminants the holes provide 16% of the area of the first filter surface 23.

Pooling in the corner region 25 enables a relatively small amount of sample material to accumulate to a greater depth, thereby increasing the tendency of the liquid to pass through the holes by gravity. The corner region 25 is also the region where a relatively large number of the holes are disposed, since the holes are provided in groups of holes each arranged relatively further from the corner and at a higher point on the first filter surface. 23. However, to maintain good filter throughput when a large volume of sample material is present, or when the holes in the corner region are obstructed by larger particles that cannot pass there-through, the first filter element 23 angles upwardly away from the wall, to enable a greater volume of sample material to be exposed to the first filter surface 23.

As can be appreciated from FIGS. 1-4, the first filter element 23 is provided as an insert arranged in a container 30 in which the sample is to be provided. The first filter element 21 is provided as push-fit in the container to, to retain the first filter element 21 in the container 30 and as explained in more detail below to contact a second filter element 22 and to thereby also retain the second filter element 22 in the container 30. The second filter element 22 is also provided as an insert in the container 30. The first filter element 21 comprises a leg 26 extending down below the first filter surface 23 and arranged in contact with the second filter element 22 and to hold the second filter element in place.

The second filter element 22 is provided in the sample collection apparatus 1 to work with the first filter element 21 as part of the filter assembly 20. The output side of the first filter element 21 is in fluid communication with the input side of the second filter element 22. Following removal of relatively larger particulate from the sample by the first filter element 21 the second filter element 22 is arranged to separate out relatively smaller particulates from a sample by action of gravity drawing the liquid component through the second filter element 22. The second filter element 22 comprises a plug of fibrous wadding material.

Only particulate matter below a predetermined threshold remains with the filtered liquid component in the output of the second filter element 22, which also comprises the output of the filter assembly 20. Material that passes through the first filter element 21 can accumulate and be held in a buffer volume between the first filter element 21 and the second filter element 22 when the rate of passage of material through the first filter element 21 is greater than the rate of passage of material through the second filter element 22. As can be appreciated from the FIGS. 2 and 3C, the second filter element 22 comprises a smaller cross sectional area than the first filter element 21, but a greater vertical depth. Reduction of the cross sectional area in this way provides an increased depth of liquid in a buffer volume between the output side of the first filter element 21 and the input side of the second filter element 23. Thus the narrow cross section of the buffer volume serves to increase passage of material through the second filter element 23.

The output of the filter assembly is provided from the second filter element to accumulate in a collection space there-below. The accumulation of sample material in the collection space may then be delivered to an assay unit as described in more detail below with reference to FIGS. 2, 5 and 6. In the embodiments described above the collection space 40 is provided with one or more ventilation openings 32 by which air from within the collection space may vent. In the example shown in FIGS. 1-3 three ventilation openings 32 are provided around the container 30 at 120 degree separation from each another. The ventilation openings 32 are provided so that air from within the collection space 40 can exit the container, making space for the sample to pass into the collection space 40.

The sample collection apparatus shown comprises an interface 50 between the collection space 40 and the assay unit 60. The interface 50 is arranged to transform from a closed configuration in which the collection space 40 is isolated from the assay unit 60 to an open configuration in which a sample accumulated in the collection space 40 is delivered to the assay unit 60. The assay unit 60 may be provided with an assay solution or reagent that is used to evaluate the constituents or other characteristics of the sample, such as by a colour change reaction which is visible through a transparent wall portion of the assay unit. Maintaining the reagent separate from the sample, by providing the interface 50 ensures that the correct reaction can take place between the sample and the reagent, and that the reaction takes place at a time where its outcome can be observed.

The collection space 40 and assay unit 60 are arranged relative to one another such that delivery of the sample to the assay unit 60 takes place under the influence of gravity. The base of the assay unit 60 enables the sample collection apparatus to stand on a flat surface and for the filtering and delivery of the sample to take place without the need for centrifugation.

To assist in delivery of the sample to the assay unit 60 the assay unit is provided as a closed volume, for example comprising a reagent and a region of low pressure. A partial vacuum can be used such that the contents of the assay unit 60 are kept at lower than atmospheric pressure. In this way, transformation of the interface 50 from the closed configuration to the open configuration exposes the low pressure region of the assay unit 60 to the collection space 40. The low pressure then acts with the atmosphere so contents of the collection space 40, including at least part of the sample, are forcibly delivered to the assay unit 60. It is desirable, as explained below, that the low pressure region of the assay unit 60 is connected to a portion of the collection space such that the sample fills the connection passageway and that therefore the sample is delivered into the low pressure region rather than air bypassing the sample.

As shown in FIGS. 5A through 5D, the collection space 40 comprises three containers of metered volume 42 and an overflow container 44. The assay unit comprises a plurality of assay volumes 62 corresponding to the metered volumes 42 of the collection space 40. The metered volumes 42 each comprise an outlet passageway the assay volumes 62 each comprise an inlet passageway. Transforming the interface 50 from the closed configuration to the open configuration comprises bringing the metered volumes and assay volumes from an unaligned position to an aligned position, such that their respective passageways connect with one another, by relative rotation of the collection space 40 and the assay unit 60. A relative rotation in the reverse sense takes the passageways back to the unaligned positions so that the collection space and assay unit are again isolated from one another at the interface, thereby preventing any further sample material having an effect on the content of the assay unit.

The transformation of the interface as described exposes the low pressure region of the assay unit 60 to the collection space 40 via a lowermost portion of the collection space 40, such that contents of the lowermost portion are forcibly delivered to the assay unit 60. In fact the contents of the metered volumes 42 are forcibly delivered to the assay unit since the outlet passageways of the metered volumes comprise the lowermost portion of the collection space from which sample material can be delivered to the assay unit 60.

In use the metered volumes are arranged to fill with sample material delivered from the second filter element 22, and then overflow into the overflow container 44. This means that a full metered volume 42 delivers no more than the volume thereof to the assay unit 60. In corresponding manner the assay volumes 62 may be pre-loaded with a measured amount of reagent to react with the sample material delivered thereto from the metered volumes 42, for example with different reagents in different assay volumes 62, or the same reagent provided more than once to give a control or supplementary check.

In the embodiments shown the collection space 40 and assay container 60 are provided with a seal 52 at the interface 50 there-between. The seal 52 works with a mechanical connection 54 by which the collection space 40 and assay container 60 are coupled to one another. The seal 52 is provided as a gasket with holes therein, by which the passageways may connect, for example a gasket formed of a plastics material or a natural or synthetic rubber material.

Figure 6:
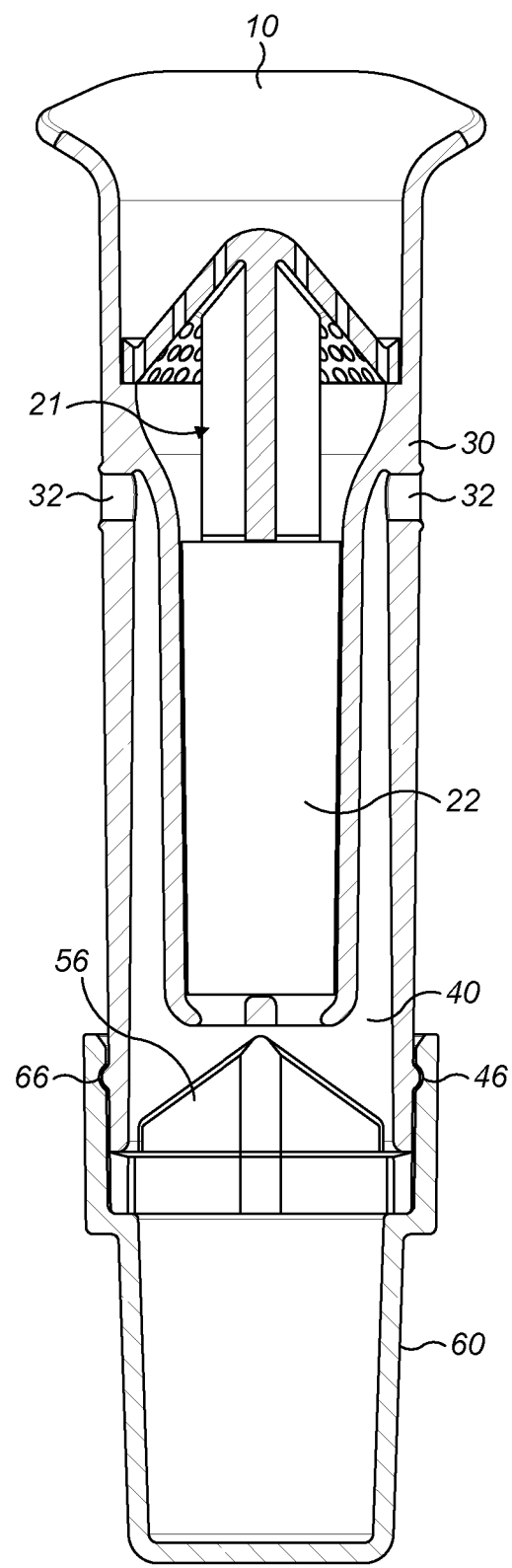
FIG. 6 shows a cut-away view of still another example sample collection apparatus.

FIG. 6 shows an example embodiment in which a frangible sealing member has been provided as the interface 50. The frangible sealing member (not shown) is provided on the collection space 40 and serves to close the bottom of the collection space 40. The assay unit 50 comprises a piercing member 54 arranged to break open a frangible sealing member in the process of transformation of the interface from the closed configuration to the open configuration. The piercing member 56 is arranged to push through the frangible sealing member as the collection space 40 and assay unit 60 are pushed together to mechanically connect one to the other. In the embodiment of FIG. 6, it is clear how the pushing together of the assay unit 60 and collection space 40 forms a mechanical connection by a recess 66 on an interior wall of the assay unit 60 cooperating with a projection 46 extending from an exterior wall of the container 30 in the region of the collection space 40. In another embodiment the interface 50 further comprises a frangible sealing member (not shown) provided on the assay unit 60 to close the top of the assay unit 60. In such embodiments the interface may is for example provided by the two frangible sealing members, with the end region of the collection space breaking the frangible sealing member on the assay unit 60 as the end region of the collection space enters the assay unit 60, and a piercing member associated with the assay unit 60 breaking the frangible sealing member on the collection space also as the end region of the collection space. As will be appreciated, a piercing member may be provided in the collection space, and the transformation of the interface by breaking of frangible sealing members may take place with the features of assay unit and collection space at the interface reversed from the embodiments described above. It will be understood that frangible sealing members used in these embodiments are preferably made from a material which can be pierced, or otherwise breached without disintegrating into fragments, so as to avoid contamination of the sample. Polymeric films, laminated foils etc. are suitable, and may be provided with inbuilt lines of weakness such as by scoring in order to facilitate operations as described above.

Figure 7B:
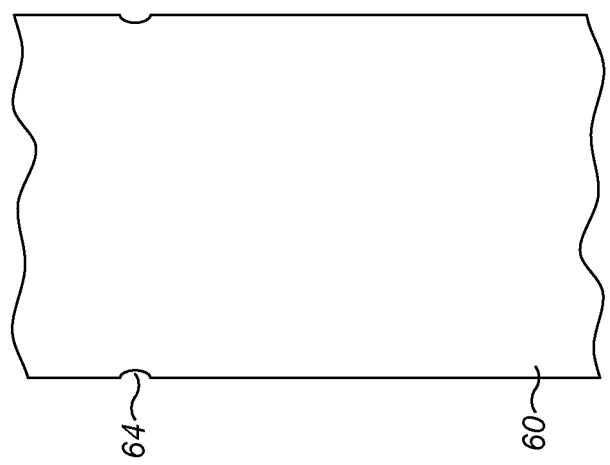
FIG. 7 shows a cut-away view of a ventilation closing arrangement of still yet another example sample collection apparatus.
Figure 7A:
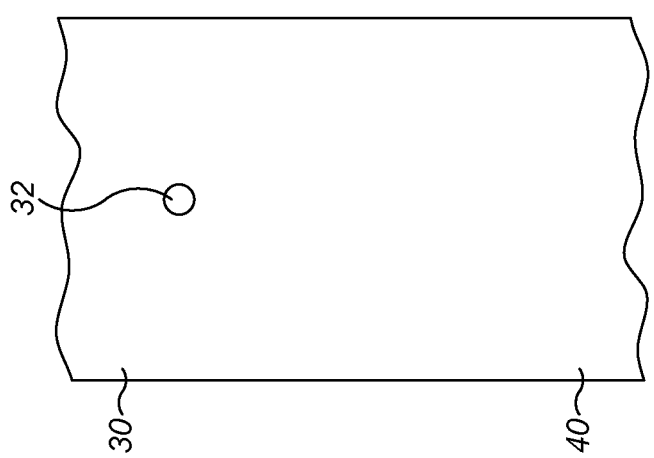

FIG. 7A and FIG. 7B show an example embodiment in which the container 30 that provides the collection space 40 and assay unit 60 comprise a mechanical connection by which they may be coupled to one another, said mechanical connection including providing a ventilation blocking members 64 on the assay unit 60 to block ventilation openings 32. Blocking the ventilation openings once the mechanical connection has been made between the collection space 40 and the assay unit 60 is useful for two reasons. Firstly, it prevents sample material from leaking out of the ventilation openings 32 if the sample collector is knocked over or otherwise tipped onto its side. Secondly, in embodiments where the assay unit 60 is at lower than atmospheric pressure, it prevents air from entering the ventilation openings as the region of reduced pressure in the assay unit 60 is exposed to the collection space 40 on transformation of the interface 50. This means that there is more chance of sample material being transferred into the assay unit 60 from the collection space, and/or means that sample material in the filter assembly is drawn through to the collection space for delivery to the assay unit 60.

FIG. 8A shows an example method of sample collection using a sample collection apparatus comprising an open ended container to receive a sample from a user. At S110, a projecting surface that extends generally outwardly and upwardly from the open end of the container to form an ergonomic lip engaging portion is arranged against the body of the user at or below the lip of the user. At S120, drool from the user is collected into the container, from the projecting surface. Step S110 may be understood to further include the step of arranging a contact region of the lip engaging portion in contact with the body of a user in alignment with a median plane of the body of the user.

FIG. 8B shows an example method of sample filtering using a filter assembly for filtering samples of saliva, and comprising a first filter element arranged to separate relatively large particulate matter from a sample, by action of gravity drawing the relatively smaller particulate matter and liquid components through the first filter element. At S210, a sample of saliva is collected by pooling of the collected sample in a corner region between an upwardly angled first filter surface of the first filter element and a wall. At S220, the relatively large particulate matter is separated from a sample, by action of gravity drawing the relatively smaller particulate matter and liquid components through the first filter element.

S210 may be preceded by steps S110 and S120 described in relation to FIG. 8A.

FIG. 8C shows an example method of using a sample collection apparatus. At S310, a sample is accumulated in a collection space of a sample collection apparatus. At S320, an interface between the collection space and an assay unit is transformed from a closed configuration in which the collection space is isolated from the assay unit, to an open configuration. At S330, the sample accumulated in the collection space is delivered to the assay unit.

Where the collection space comprises an outlet passageway and the assay unit comprises an inlet passageway, S320 may be expanded to include the step of bringing the passageways from an unaligned position to an aligned position in transforming the interface between the collection space and assay unit by relative motion there-between, for example by relative rotation of the collection space and assay unit.

S330 may be expanded to include the step of filling a container of metered volume in the collection space with material of the sample, and collecting further material of the sample in an overflow container so that delivering material of the sample from the collection space takes place into one, or into a plurality of assay volumes in the assay unit.

S310 may be preceded by the step of pre-loading the assay unit with a reagent.

S330 may be followed by the step of mixing of a sample with a reagent in the assay unit, and thereafter inspecting the content of the assay unit while the sample is contained therein.

As set out above, the sample collection apparatus aims to provide a convenient way for a saliva sample to be received. It will be understand that the saliva sample as discussed may contain entrained sputum or other material delivered from the mouth of the user so as not to be comprised completely of material produced by the salivary glands. However, this does not impact on the use or general efficacy of the embodiments. The sample collection can be in a clinical setting, under guidance from a healthcare professional, or, as will be appreciated the method of use is simple enough to be undertaken without supervision yet a good quality sample and assay output can still be achieved. The risk of spillage is reduced, as is wastage of saliva in wetting surfaces and filter components. The collected sample is filtered effectively, and can be delivered in a proper clean and timely manner to an assay unit for analysis without the need for centrifugation, and without the risk of contamination or spillage.

In addition to the advantages and improvements in each functional unit/operational process of collecting a sample, it will be appreciated that the functional units/operational processes work together to enable the end-to-end collection and processing of a sample in a single device.

Although the example embodiments have been described with reference to the components, modules and units discussed herein, such functional elements may be combined into fewer elements or separated into additional elements.

Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" may mean including the component(s) specified but is not intended to exclude the presence of other components.

Although a few example embodiments have been shown and described, it will be appreciated by those skilled in the art that various changes and modifications might be made without departing from the scope of the invention, as defined in the appended claims.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

We claim:

1. A sample collection apparatus comprising a filter assembly to filter samples of saliva collected therein, the filter assembly comprising:
   a first filter element arranged to separate relatively large particulate matter from a sample, by action of gravity drawing the relatively smaller particulate matter and liquid components through the first filter element,
   the first filter element comprises an upwardly angled conical or frustoconical first filter surface, arranged with a wall, to pool the sample in a corner region between the first filter surface and the wall;
   wherein the filter assembly comprises a second filter element; and
   wherein the first and second filter elements are arranged in the filter assembly such that the output side of the first filter element is in fluid communication with the input side of the second filter element, and wherein the second filter element is arranged to separate relatively small particulate matter from a sample, by action of gravity drawing the liquid component through the second filter element such that only particulate matter below a predetermined threshold remains with the filtered liquid component.

2. The filter assembly according to claim 1, wherein the filter assembly is arranged with a buffer volume between the output side of the first filter element and the input side of the second filter element.

3. The filter assembly according to claim 1, wherein the first filter surface is provided as part of an upwardly extending first filter element.

4. The filter assembly according to claim 1, wherein the first filter element comprises a plurality of discrete filter holes.

5. The filter assembly according to claim 1, wherein the first filter surface comprises a first group of holes arranged relatively closer to the corner, and a second group of holes arranged relatively further from the corner.

6. The filter assembly according to claim 1, wherein the first filter element is provided as an insert arranged in a container in which the sample is provided.

7. The filter assembly according to claim 1, wherein the first filter element and the container are arranged, such that inserting the first filter element into the container to an inserted position causes retention of the first filter element in the container.

8. The filter assembly according to claim 1, wherein the wall is provided, at least in part, by an opposed portion of the first filter element, providing an upwardly angled surface that extends from the corner region away from the first filter surface.

9. The filter assembly according to claim 1, wherein the wall is provided, at least in part, by the container in which the sample has been collected.

10. The filter assembly according to claim 1, wherein the second filter element is made of a fibrous material.

11. The filter assembly according to claim 1, wherein the second filter element is provided as an insert arranged in a container in which the sample is provided.

12. The filter assembly according to claim 1, wherein the first filter element, second filter element and container are arranged, such that inserting the first filter element into the container to an inserted position causes retention of the second filter element in the container.

13. A method of filtering saliva in a sample collection apparatus, the method performed using a filter assembly of the sample collection apparatus comprising
   a first filter element arranged to separate relatively large particulate matter from a sample, by action of gravity drawing the relatively smaller particulate matter and liquid components through the first filter element, and
   a second filter element arranged such that the output side of the first filter element is in fluid communication with the input side of the second filter element and the second filter element is arranged to separate relatively small particulate matter from the sample, by action of gravity drawing the liquid component through the second filter element such that such that only particulate matter below a predetermined threshold remains with the filtered liquid component,
the method comprising collecting a sample of saliva, and characterised by pooling the collected sample in a corner region between an upwardly angled conical or frustoconical first filter surface of the first filter element and a wall.

14. The method of filtering according to claim 13, the method performed using the filter assembly provided in a container, the method comprising arranging the container to rest on a level surface with the first filter surface as an upwardly angled first filter surface, and/or the wall extending generally upwards vertically.

* * * * *

UNITED STATES PATENT AND TRADEMARK OFFICE
CERTIFICATE OF CORRECTION

PATENT NO. : 10,390,804 B2
APPLICATION NO. : 15/320690
DATED : August 27, 2019
INVENTOR(S) : Monica Silverstone Spiteri and Neil Patel It is certified that error appears in the above-identified patent and that said Letters Patent is hereby corrected as shown below:

On the Title Page

In the Title and in the Specification, Column 1, Line 1, the words --IMPROVEMENTS IN AND RELATING TO-- should be added to the beginning Signed and Sealed this
Nineteenth Day of November, 2019

Andrei Iancu
*Director of the United States Patent and Trademark Office*